United States Patent [19]

Mozes et al.

[11] Patent Number: 5,356,779
[45] Date of Patent: Oct. 18, 1994

[54] ASSAY FOR DIRECT BINDING OF PEPTIDES THAT ARE T-CELL EPITOPES TO MHC GENE PRODUCTS ON INTACT ANTIGEN-PRESENTING CELLS AND THE USE THEREOF FOR SCREENING SUSCEPTIBILITY OF AUTOIMMUNE DISEASES

[75] Inventors: Edna Mozes; Israel Pecht, both of Rehovot, Israel

[73] Assignee: Yeda Research and Development Co. Ltd., Rehovot, Israel

[21] Appl. No.: 624,730

[22] Filed: Dec. 10, 1990

[30] Foreign Application Priority Data

Dec. 10, 1989 [IL] Israel .................................. 92629

[51] Int. Cl.$^5$ .................. G01N 33/564; G01N 33/567
[52] U.S. Cl. .................................... 435/7.24; 435/7.21; 435/7.5; 435/7.8; 435/29; 436/503; 436/506
[58] Field of Search ................. 435/7.24, 7.5, 7.8, 435/29, 7.21; 436/503, 506

[56] References Cited

U.S. PATENT DOCUMENTS 5,200,320 4/1993 Sette et al. ................ 435/7.24

OTHER PUBLICATIONS

I. M. Roitt, *Essential Immunology*–5th Ed., Blackwell Scientific Publications, Oxford, UK, 1984, pp. 65–66.
J. B. Rothbard et al, *Internat. Immunol.*, 11, 479–486, 1989.
E. Mozes et al, *EMBO Journal*, 8, 4049–4052 (1989).
D. E. Smilek et al, *Immunol. Rev.*, 118, 37–71 (1990).
R. Busch et al, *Internat. Immunol.*, 2, 444–451 (1990).
Chemical Abstracts, vol. 112, No. 19, May 1990, p. 537, abstract No. 176542y, Columbis, Ohio, Us; E. Mozes et al. "Direct binding of a myasthenia gravis related epitope to MHC class II molecules on living murine antigen–presenting cells", & EMBO J. 1989, 8(13), 4049–52.
Nature, vol. 339, Jun. 1989, pp. 392–394, London, GB; R. Ceppellini et al. "Binding of labelled influenza matrix peptide to HLA DR in living B1 Lymphoid cells".

*Primary Examiner*—David Saunders
*Attorney, Agent, or Firm*—Browdy and Neimark

[57] ABSTRACT

As assay for the measurement of direct binding of a peptide that is a T-cell epitope to gene products of the major histocompatibility complex (MHC), classes I and II, on the surface of intact living antigen-presenting cells, is provided. The assay comprises incubating the labelled peptide with the cells, and monitoring the extent of binding by the addition of a probe that reacts with the ligand used to label the peptide. The assay is suitable for autoimmune diseases and other immunological disorders. Peptides having a sequence corresponding to a stretch of the sequence of the antigen relevant to an immunological disorder, or modifications thereof, which bind to gene products of MHC, but do not stimulate T-cells, are also useful for the treatment of said disorders.

7 Claims, 5 Drawing Sheets

ASSAY FOR DIRECT BINDING OF PEPTIDES THAT ARE T-CELL EPITOPES TO MHC GENE PRODUCTS ON INTACT ANTIGEN-PRESENTING CELLS AND THE USE THEREOF FOR SCREENING SUSCEPTIBILITY OF AUTOIMMUNE DISEASES

FIELD OF THE INVENTION

The invention provides a general method for detection of, and measurement of binding of peptides, that are T-cell epitopes, to gene products of the major histocompatibility complex (MHC), classes I and II, on the surface of intact antigen- presenting cells (APC). The invention has applications in both basic and clinical research related to diseases that are regulated by T-cells. It can be utilized to screen for pathogenic epitopes in protein sequences or any other antigenic entities. In addition, it provides a technique for the rapid screening for relevant pathogenic epitopes in individual patients, and it is useful for detecting individuals at risk for developing certain immunological disorders, such as autoimmune disorders. The invention further relates to therapeutic agents that will interfere with the binding to MHC gene products and thus, inhibit T-cell responses that are relevant to the disease.

PRIOR ART

Helper T cells recognize mostly denatured or partially degraded antigens in association with class II (Ia) MHC gene products on the surface of APC. Therefore, inability of T-cells to respond to a certain peptide (epitope) within an antigen can be due to lack of binding of the peptide to either the MHC gene products, or to the T-cell antigen receptor. The association of immunologically active peptides with different MHC gene products has so far been demonstrated in binding studies of such peptides to solubilized, purified molecules of class I and class II MHC gene products, and was shown to correlate with the ability of specific class II alleles to restrict the T-cell response to specific peptides (1–5). Although recent reports have shown direct binding of a radiolabelled T-cell epitope to human MHC class II gene products on HLA homozygous, Epstein-Barr virus transformed, B cell lines (6), direct binding of T-cell epitopes to MHC class II proteins on intact living APC has not yet been demonstrated. The parenthetical numbers referred to above and throughout the present specification refer to the documents listed in the "REFERENCES" section of the present specification.

SUMMARY OF THE INVENTION

The present invention provides a direct assay for detection of, and measurement of the binding of peptides, that are T-cell epitopes, to MHC gene products on the surface of intact cells such as APC.

The invention relates to an assay for the measurement of direct binding of a peptide, that is a T-cell epitope, to gene products of the major histocompatibility complex (MHC), classes I and II, on the surface of intact living antigenpresenting cells, which comprises:

i. labelling the peptide with a ligand;

ii. incubating intact antigen-presenting cells with the labelled peptide, thus directly binding the peptide to the cells, and iii. monitoring the extent of binding by the addition of a probe that reacts with the ligand, and measuring peptide-bound cells versus peptide-unbound cells.

The ligand-probe pairs may be biotin-avidin, hapten-antibody, sugar-lectin, or any other suitable complex, and the monitoring is performed by measuring fluorescence, luminescence, radioactivity, color, etc., according to the complex ligand-probe used.

The invention involves, for example, labelling, such as biotinylation of the peptide epitope of concern, incubation of the APC with the labelled peptide for a required time period (e.g. twenty-hours for biotinylated specimens), and monitoring of the binding by flow cytometric analysis when using fluorescent conjugated streptavidin (e.g. Phycoerythrin), which forms a high affinity complex with biotin.

MHC presentation of T-cell epitopes to the antigen receptor of T-cells is a prerequisite for the specific activation of the latter cells. The concept of specific MHC gene product - T-cell epitope interactions prior to the recognition by T-cells is supported by the demonstration that epitopes can compete with one another at the level of antigen presentation by APC. However, these assays could not monitor the association directly, but rather measured the influence of the MHC-epitope interaction on T-cells specific for the relevant epitope. This is illustrated by the concrete example described below.

The invention relates to an assay for screening the susceptibility of a mammal, including humans, to an immunological disorder, wherein the peptide that is a T-cell epitope and binds to gene products of the MHC, classes I and II, has a sequence which corresponds to a stretch of the sequence of the antigen relevant to the disorder, and the extent of binding of the peptide to the antigen-presenting cells is correlated to the disease susceptibility.

The assay is suitable for autoimmune disorders, such as myasthenia gravis, certain types of diabetes, rheumatoid arthritis, systemic lupus erythematosus, multiple solerosis, etc. It may also be used to show susceptibility to other disorders, such as viral diseases.

Myasthenia gravis (MG) is a well-characterized human autoimmune disorder in which antibodies are produced that bind to nicotinic acetylcholine receptors (AChR) in the postsynaptic membrane at the neuromuscular junction. There is a significant difference in the ability of peripheral blood lymphocytes (PBL) from MG patients, in comparison to healthy controls, to proliferate in response to the synthetic peptides p195–212 and p257–269 which represent sequences of the α-subunit of the human receptor for acetylcholine (HAChRα). The proliferative responses to these peptides correlate significantly with the expression of HLA-DR5 and HLA-DR3, respectively (7).

The peptide p195–212 has the sequence: Asp-Thr-Pro-Tyr-Leu-Asp-Ile-Thr-Tyr-His-Phe-Val-Met-Gln-Arg-Leu-Pro-Leu (SEQ ID No: 1) and the peptide p257–269 has the sequence: Leu-Leu-Val-Ile-Val-Glu-Leu-Ile-Pro-Ser-Thr-Ser-Ser (257–269 of SEQ ID No.: 2).

The induction of experimental autoimmune MG (EAMG) was shown to require helper T-cells. In addition, the proliferative responses of T lymphocytes to AChR are under H-2-linked Ir gene control. In the present invention it could be demonstrated that lymph node cells of various mouse strains that were primed with the HAChRα T-cell epitopes p195–212 and p259–271 binding (which was shown to induce the same immune response as p257–269), responded to different extents to these peptides in vitro. Thus, for p195–212 high (SJL, B10.S, C3H/He), intermediate (AKR, BALB/c, C57BL/6) and low (C3H.SW) responder strains could be clearly resolved, while for p259–271 only BALB/c mice responded with high efficiency to the peptide.

The peptide p259–271 has the sequence: Val-Ile-Val-Glu-Leu-Ile-Pro-Ser-Thr-Ser-Ser-Ala-Val (259–271 of SEQ ID No.: 2).

Following immunization with the Torpedo AChR, lymphocytes of SJL mice proliferated very efficiently to p195–212, whereas lymph node cells of BALB/c mice responded well to p259–271. These results demonstrated the existence of strain dependent immunodominant and cryptic regions on the autoantigen. Therefore, the epitopes specifically recognized by T lymphocytes of patients with MG also represent specific T-cell epitopes in the immune response to the AChR in mice.

An assay for the screening of susceptibility to myasthenia gravis according to the invention comprises:

i. labelling a peptide which has a sequence corresponding to a stretch of the sequence of the human acetylcholine receptor α-subunit, with a ligand;

ii. incubating the labelled peptide with antigen-presenting cells of the donor, and iii monitoring the extent of binding with a probe that reacts with the ligand.

A further embodiment of the invention is an assay comprising:

i. biotinylating the peptide p195–212 or the peptide p257–271;

ii. incubating the biotinylated peptide with peripheral blood lymphocytes of a human donor and iii. monitoring the extent of binding using phycoerythrinavidin by flow cytometry.

The following describes an illustrative assay for direct binding of a T-cell epitope to MHC class II gene products on the surface of freshly prepared murine splenic adherent cells. Since we demonstrated in the present invention that the amino acids 195–199 at the N-terminal end of p195–212 were not essential for its immunological function, in order to detect binding to APC, we therefore attached to the N-terminus a biotinyl group, to take advantage of the amplification that can be obtained by using multiple fluoresceinated streptavidin. FIG. 1 illustrates binding measurements of the biotinylated p195–212 to freshly prepared splenic adherent cells of seven mouse strains. Binding was monitored by flow cytometric analysis. As can be seen, 15% to about 60% of the cells of all the strains tested, were labelled following 20 hours incubation with the biotinylated peptide, with the exception of splenic adherent cells of C3H.SW mice which bound to a lesser extent (about 5%).

Figure 1A:
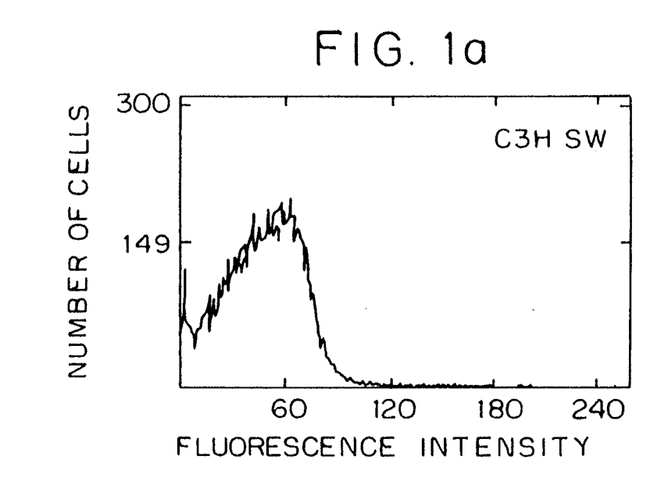
FIGS. 1a-1g: Binding of the biotinylated analog of peptide p195-212 to the surface of living splenic adherent cells of various mouse strains.
Figure 1B:
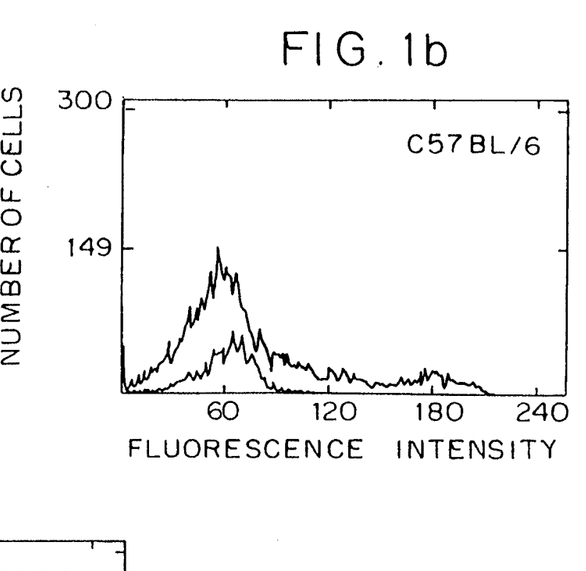
Figure 1C:
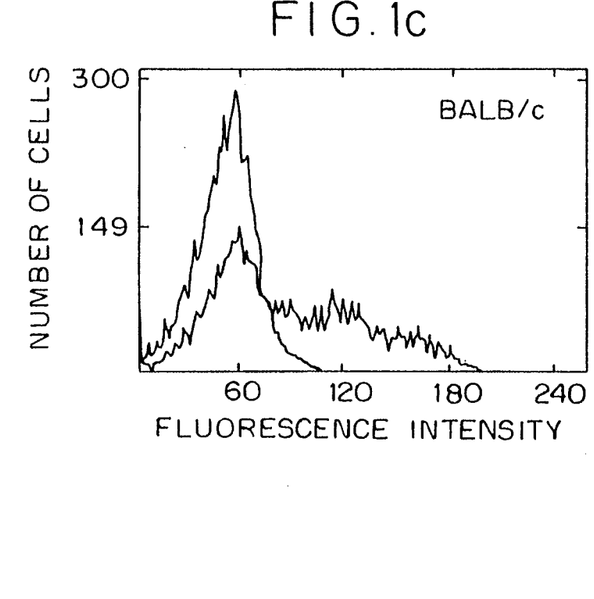
Figure 1D:
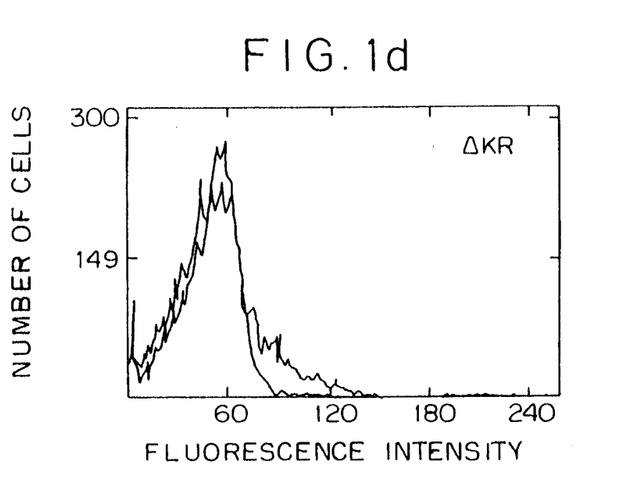
Figure 1E:
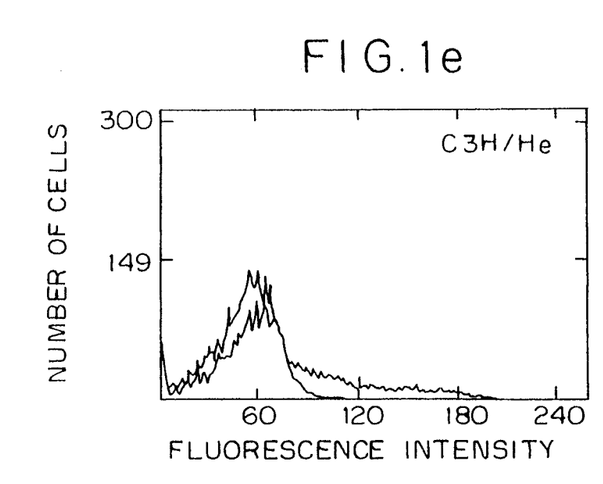
Figure 1F:
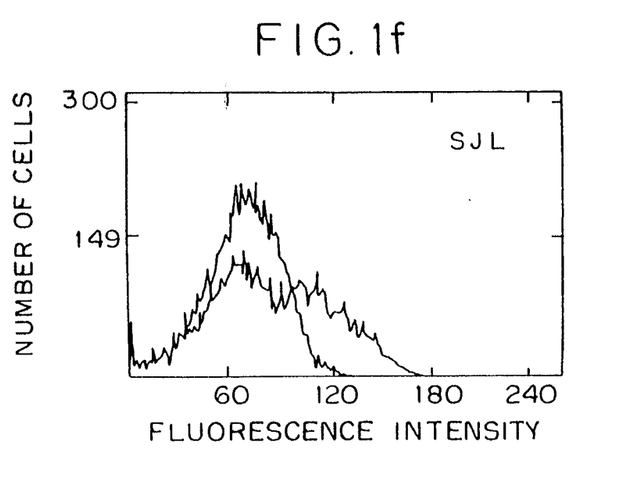
Figure 1G:
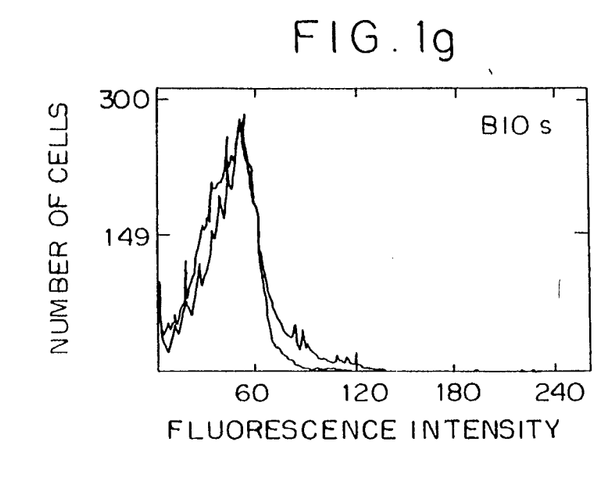
Figure 2A:
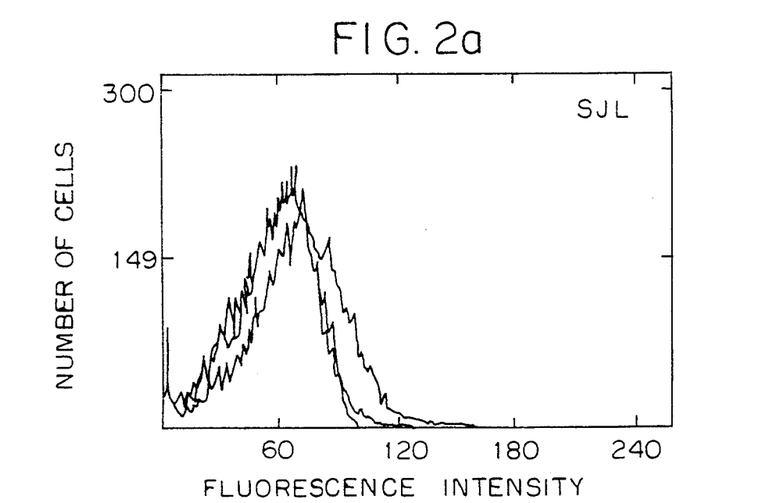
FIGS. 2a-2c: Inhibition of binding of the biotinylated p195-212 by monoclonal anti-I-A antibodies.
Figure 2B:
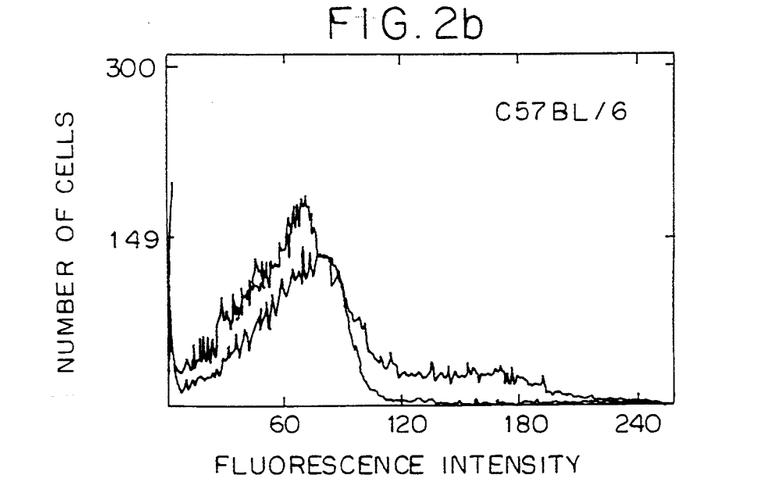
Figure 2C:
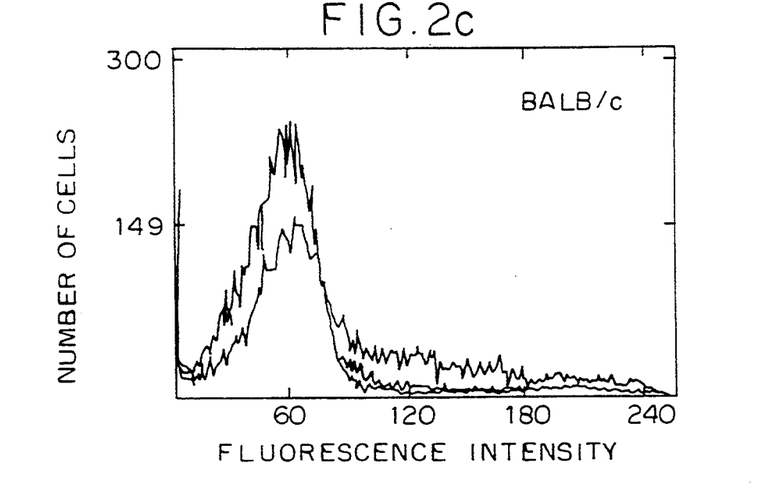

Several controls establish that p195–212 is indeed bound to MHC class II gene products on the surface of splenic adherent cells. Thus, monoclonal anti-I-A antibodies were co-incubated with the peptide in the binding experiments. FIG. 2 demonstrates that the binding of p195–212 to splenic adherent cells of various mouse strains was inhibited by the relevant monoclonal anti-I-A antibodies. The inhibition caused by the various anti-I-A antibodies was specific since, as shown in Table I, anti-I-A antibodies of irrelevant specificities did not significantly inhibit the binding of p195–212 to the MHC class II gene products. As shown in this Table, p195–212 bound to I-A molecules of the BALB/c APC since only an anti-I-A$^d$ antibody was inhibitory, whereas an anti-I-E$^a$ monoclonal antibody (14-4-4) did not cause significant inhibition.

Figure 3:
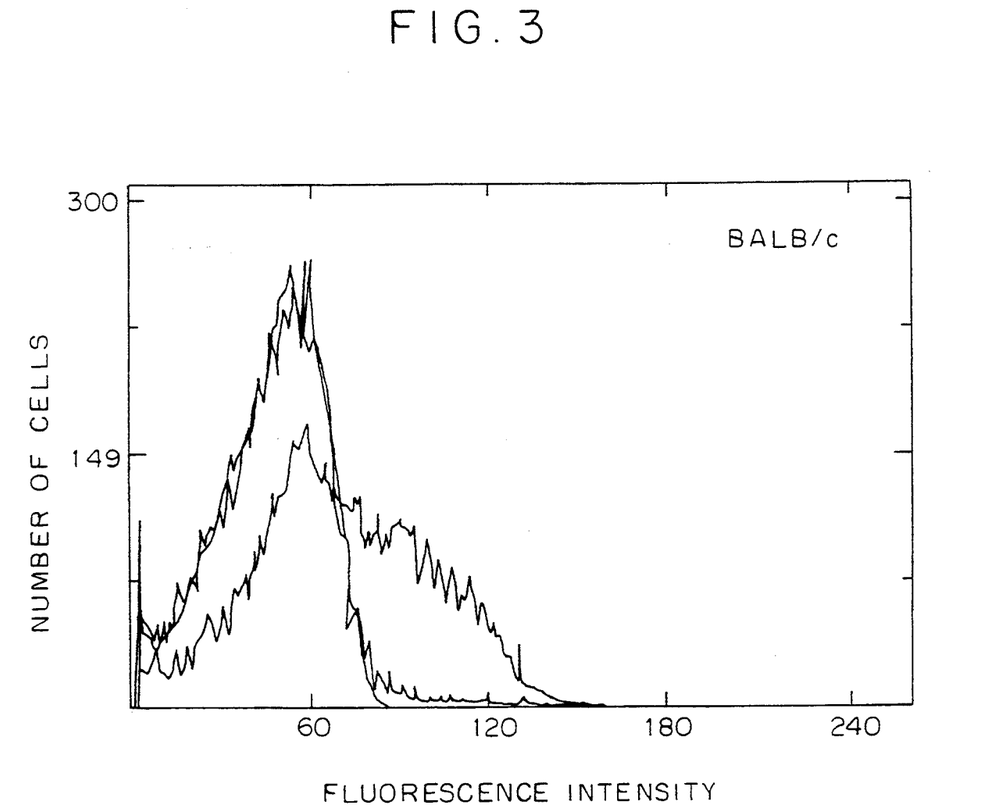
FIG. 3: Inhibition of binding of the biotinylated p195-212 in the presence of the unmodified peptide.

Another control ascertains that the biotinylated p195–212 is bound to the same site as the unmodified peptide. Hence, the splenic adherent cells of BALB/c mice were incubated with an excess of p195–212 prior to the addition of the biotinylated peptide to the incubation mixture. FIG. 3 shows that the unmodified peptide inhibited 90% of the binding and hence competes with the biotinylated peptide for the same site. Table II demonstrates that the inhibition observed with the unmodified p195–212 on BALB/c APC is specific to peptides that are Ia$^d$ restricted. The present data constitute the first direct evidence for T-cell epitopes binding to intact living murine APC. The binding of the biotinylated peptide was shown to be specific in terms of both, binding site on the cells and epitope structure.

Figure 4A:
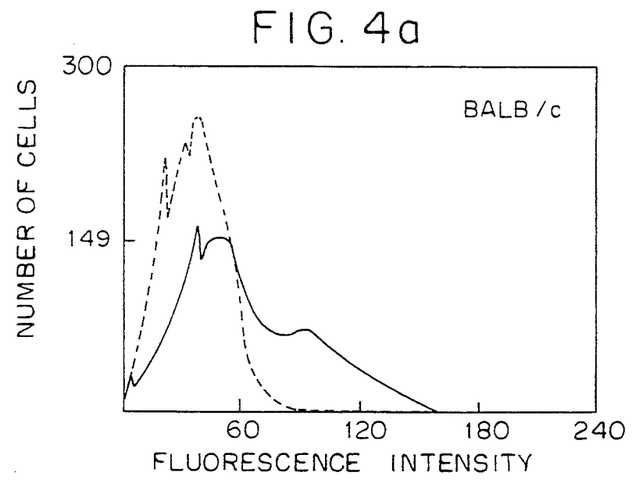
FIGS. 4a-4c Binding of the biotinylated analog of peptide p257-271 to the surface of living splenic adherent cells of various mouse strains.
Figure 4B:
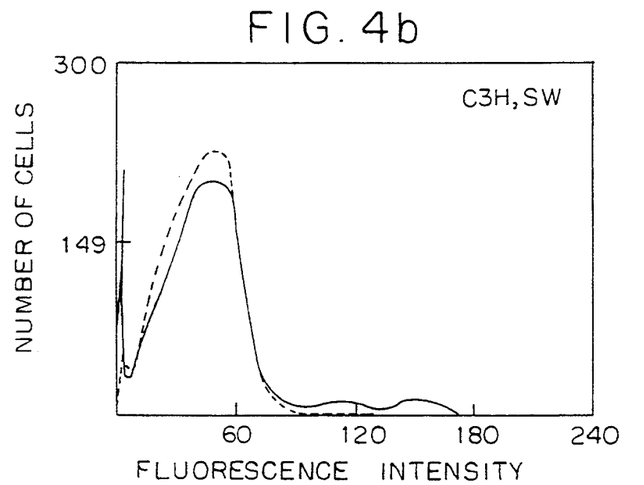
Figure 4C:
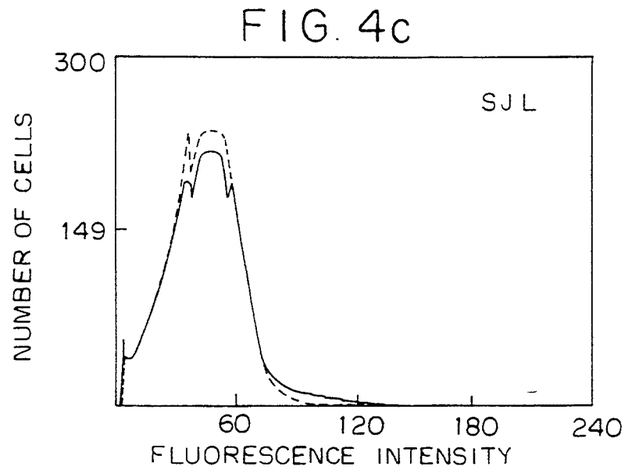

Since the peptide p257–271 can stimulate a p259–271 specific T-cell line with a potency similar to p259–271, we attached biotin to the N-terminus of p257–271, assuming that the leucine at position 257 is not essential for the binding to MHC gene products. FIG. 4 demonstrates the binding of biotinylated p257–271 to 3 inbred mouse strains. Only BALB/c mice bound this peptide to high extent (39%). These results indicate that the extent of binding can be correlated to biological responses, such as lymph nodes proliferation assays from mice primed with the relevant peptide.

Further studies showed that APC of an HLA-DR5 individual whose PBL proliferated in response to p195–212 also bound the same biotinylated peptide. Therefore, this invention is applicable to human cells as well.

The studies described above were performed with peptides derived from the HAChRα autoantigen, in order to shed light on the mechanisms involved in autoimmunity. In MG and other helper T-cell mediated autoimmune diseases, an autoantigen is processed and presented by APC to T-cells. The T-cell activation initiates a cascade of events, including proliferation of T-cells, secretion of lymphokines, and specific help for B-cells to produce autoantibodies.

The invention provides a direct binding assay that is simple to perform, especially as flow cytometers become standard clinical equipment. It is less time consuming and demands a smaller amount of cells in comparison to proliferation assays or to bioassays that determine lymphokine production. Moreover, this method is reproducible, accurate and does not require repeated calibrations. In addition, with the appropriate kit, this method may be applied routinely in both clinical and research laboratories.

The invention provides a general method for detection and measurement of binding of peptides that are T-cell epitopes to MHC class II and class I gene products on the surface of APC. The method is useful in studies of diseases that are regulated by T-cells. It has applications in both basic and clinical research: (1) Screening for pathogenic epitopes in protein sequences. (2) Rapid screening for the relevant pathogenic epitopes in individual patients. (3) Detection of individuals at risk for developing a certain disease. (4) Development of therapeutic agents that will interfere with the binding to MHC proteins and thus, inhibit T-cell responses that are relevant to the disease, instead of the non-specific T-cell inhibition achieved today with medications such as cyclosporine A.

EXAMPLES

1) Preparation of the N-Terminal biotinylated peptide p195-212

1.1 mg of p195-212 (or an equivalent amount of the other peptides) was dissolved in 0.5 ml of aqueous 0.1M $NaHCO_3$. When necessary 30 µl 0. M NaOH was added in order to achieve complete solubilization. The solution was cooled in ice. Biotin-N-hydroxy-succinimide (BNHS) was added to 30% molar excess [133 µg/[133 µl a, N-dimethylformamide (DSMF)]. The reaction was allowed to proceed at 0° C. for 2 h. Since excess of unreacted BNHS is hydrolyzed in the reaction mixture, it does not interfere with binding to the cells and therefore no further purification of the conjugate was performed.

Detection of the bound T-cell epitope is achieved by monitoring a fluorescent probe having a stable link with the epitope. Several alterations can be used; (1) Direct covalent conjugation of the epitope to a fluorescent probe, as exemplified by phycoerythrin and its analogues. Low molecular weight probes may also be used whenever their fluorescent properties are satisfactory. Examples of the latter are coordination compounds of luminescent ions, e.g. lanthanides such as Europium. (2) Non-covalent-high affinity complexes between the appropriate fluoresceinated binding reagent and a ligand attached covalently to the T-cell epitope. Examples of such systems are: (1) Biotin conjugated to the T-cell epitope and avidin (or analogues) conjugated to phycoerythrin (or analogues). (2) A hapten conjugated to the epitope and a high affinity antibody carrying fluroescent probes on it.

2) Direct binding of Peptides to Murine APC

Murine spleen cells ($1\times10^6$) suspended in RPMI and supplemented with 10% fetal calf serum are incubated in Petri dishes for one hour at 37° C. Thereafter, non-adherent cells are removed and the plates are washed three times with RPMI and placed on ice. Adherent cells are collected from the plates using a rubber policeman.

Splenic adherent cells ($1\times10^6$/sample) are incubated with a biotin-conjugated peptide (50 µM) in phosphate buffered saline containing 0.1% bovine serum albumin (PBS/BSA), at 37° C. for twenty hours, followed by incubation with phycoerythrin (PE)-streptavidin at 4° C. for thirty minutes. After each incubation the cells are washed twice at 4° C. with the PBS/BSA solution. Thereafter, cells are analyzed by flow cytometry. In each analysis minimally $10^4$ cells are examined.

3) Direct binding of Peptides to Human APC

Peripheral blood lymphocytes (PBL) of human individuals are isolated from the whole blood by Ficoll-Hypaque density gradient centrifugation. The PBL obtained are treated in the same manner as the murine spleen cells.

4) A Screening Kit for Pathogenic Epitopes of Human Individuals

A representative kit contains biotinylated peptides that represent sequences from the HAChRa and are relevant to the disease myasthenia gravis. PBL cells are isolated from blood samples of human individuals and adhered according to the procedure described under Example 2. $1\times10^6$ of the adherent cells are placed in tubes. The various biotinylated peptides in the kit are distributed in 50 µl aliquotes to the different tubes. A control tube without a biotinylated peptide is added to each experiment. The tubes are vortexed for ten seconds and then incubated at 37° C. After twenty hours the samples are washed twice, incubated with Phycoerythrin-streptavidin at 4° C. for thirty minutes, washed twice again, and subjected to flow cytometric analysis.

5) Immunotherapy with Biotinylated Peptides

Peptides having a sequence corresponding to a part of the amino acid sequence of the antigen relevant to a certain immunological disorder, which bind to MHC gene products but do not stimulate T-cells, are useful for therapy of the same disorder. As illustrative examples, the peptides p195-212, p257-271 and p259-271 disclosed herein are suitable for treatment of myasthenia gravis.

Also peptides with modification of the amino acids in their sequence, which behave in a similar way, i.e., interact with gene products of MHC, classes I and II, on the cell surface, and do not stimulate T-cells, may be useful in therapy and their use is encompassed by the present invention. These modifications include derivatives of the amino acids or replacement of the amino acids comprised within the peptide sequence by other suitable amino acids. The biotinylation or other similar derivatization of the peptide may improve its efficacy.

Substitutions of critical amino acids in the peptides make it possible to identify peptides that bind with high affinity to the MHC gene products, and thereby block the interactions with the pathogenic autoantigens.

The biotin moiety is a vitamin that is essential for life. Hence, its conjugation with a peptide that blocks certain MHC alleles is clinically safe. Therefore, substituted derivatives of the pathogenic peptides that interact with the MHC gene products, but do not stimulate the T-cells that are associated with the autoimmune disease, will be used in therapy, preferably in a biotinylated form.

Mice with autoimmune response will be injected with a physiologic solution containing 50-500 µg of the relevant biotinylated derivatives twice a week.

The invention further relates to pharmaceutical compositions for preventing or alleviating effects of pathogenic peptide autoantigens which bind to MHC gene products and cause an autoimmune disorder, comprising as active ingredient an effective quantity of a biotin- or otherwise- substituted derivative of such pathogenic peptide, or other modification thereof, adapted to interact with the MHC gene product but not to stimulate T-cells.

FIGURE LEGENDS

Splenic adherent cells ($1\times10^6$/100 µl) were incubated with the biotinylated p195-212 (50 µM) for 20 hours and stained with phycoerythrin-streptavidin (0.5 µg). (—), staining of cells incubated with the biotinylated p195-212; (...), background fluorescence in the absence of biotinylated peptide.

Splenic adherent cells ($1\times10^6$/sample) were co-incubated with the biotinylated p195-212 (50 µM) and the different monoclonal anti-I-A antibodies (0.3 nM), for 20 hours, and stained thereafter with phycoerythrin-streptavidin. (—), staining of the cells incubated with the biotinylated p195-212; (—.—.—.), staining of the cells incubated with both the biotinylated p195-212 and the monoclonal anti-I-A antibodies; (...), background fluorescence in the absence of biotinylated peptide.

Splenic adherent cells (1×10⁶ cells/100 μl) were incubated with an excess (20-folds) of the unmodified p195-212 for 3 hours prior to the addition of the biotinylated p195-212 (50 μM). Phycoerythrin-streptavidin (0.5 μg) was added thereafter. (—), staining of the cells incubated with the biotinylated p195-212; (—.—.—.), staining of the cells incubated with an excess of the unmodified peptide; (...), background fluorescence in the absence of biotinylated peptide.

Splenic adherent cells (1×10⁶/100 μl) were incubated with the biotinylated p257-271 (50 μM) for 20 h and stained with phycoerythrin-streptavidin (0.5 μg), (— — —), staining of cells incubated with the biotinylated p-257-271; (—) background fluorescence in the absence of biotinylated peptide.

REFERENCES

1. Babbit et al., Nature 317, 359-361 (1985).
2. Buus et al., Cell 47, 1071-1077 (1986).
3. Guilllet et al., Nature 324, 260-261 (1986).
4. Watts et al., Proc.Natl.Acad.Sci.USA 83, 9660-9664 (1986).
5. Chen et al., Nature 337, 743-745 (1989).
6. Ceppellini et al., Nature 339, 392-394 (1989).
7. Brocke et al., J. Clin. Invest. 82, 1894-1900 (1988).

TABLE I

Inhibition of p195-212 binding to APC of different mouse strains using monoclonal anti Ia antibodies

| Strain | H-2 | mAb used | % inhibition |
|---|---|---|---|
| C57BL/6 | b | α I-A$^{b,d}$ (34-5-3) | 90 |
|  |  | α I-A$^d$ (MKD6) | 0 |
| BALB/c | d | α I-A$^d$ (MKD6) | 89 |
|  |  | α I-E$^d$ (14-4-4) | 14 |
| SJL | s | α I-A$^{s,b}$(Y3P) | 100 |
|  |  | α I-A$^d$ (MKD6) | 19 |

The monoclonal anti I-A antibodies were added (0.3 nM final concentration) to the APC together with the biotinylated peptide for 20 hours of incubation. Phycoerythrin-streptavidin was added thereafter and the cells were subjected to flow cytometric analysis. All mAbs employed were of the IgG$_{2a}$ isotype.

TABLE II

Binding of bioninylated p195-212 to BALB/c APC in the presence of various unmodified peptides.

| APC | Biotinylated p195-212 (50 μM) | Unmodified peptide | Percent binding |
|---|---|---|---|
| + | — | — | 8.9 |
| + | + | — | 51.4 |
| + | + | Human AChR 195-212 | 11.7 |
| + | + | Torpedo AChR 12-26 | 9.6 |
| + | + | Myelin Basic Protein 90-101 | 49 |

Splenic adherent cells of BALB/c mice were incubated with an excess of the unmodified peptides (20-fold over the biotenylated p195-212) for 3 hours prior to the addition of the biotinylated peptide. Phycoerythrin-streptavidin was added thereafter and the cells were subjected to flow cytometric analysis. The biotinylated peptide with sequence 90-101 of the myelin basic protein yielded 11% binding to BALB/c APC.

We claim:

1. An assay for screening the susceptibility of a mammal to an immunological disorder, comprising:
   labelling with a ligand a peptide that is a T-cell epitope having a sequence corresponding to a stretch of the sequence of the antigen relevant to the disorder and binds to gene products of the major histocompatibility complex (MHC), classes I and II, on the surface of intact living antigen presenting cells;
   incubating intact living antigen-presenting cells with the labelled peptide, thus directly binding the peptide to the cells; and
   monitoring the extent of binding by the addition of a probe that reacts with the ligand and measuring peptide bound cells versus peptide-unbound cells, whereby the extent of the binding of the peptide to the antigen-presenting cells is correlated to the susceptibility to the disorder.--

2. An assay according to claim 1 wherein the ligand-probe pairs are selected from the group consisting of biotin-avidin, hapten-antibody and sugar-lectin.

3. An assay is accordance with claim 1, wherein said mammal is a human.--

4. An assay according to claim 1 for the screening of susceptibility to autoimmune disorders.

5. As assay according to claim 4 for the screening of susceptibility of a subject to myasthenia gravis, which comprises:
   i. labelling a peptide which has a sequence corresponding to a stretch of the sequence of the human acetylcholine receptor α-subunit;
   ii. incubating the labelled peptide with antigen-presenting cells of the subject, and
   iii. monitoring the extent of binding with a probe that reacts with the ligand.

6. An assay according to claim 5, wherein the subject is a human subject, which comprises:
   i. biotinylating the peptide p195–212 of the sequence: Asp-Thr-Pro-Tyr-Leu-Asp-Ile-Thr-Tyr-His-Phe-Val-Met-Gln-Arg-Leu-Pro-Leu (SEQ ID NO: 1) or the peptide p257–271 of the sequence: Leu-Leu-Val-Ile-Val-Glu-Leu-Ile-Pro-Ser-Thr-Ser-Ser-Ala-Val (SEQ ID NO: 2);
   ii. incubating the biotinylated peptide with the antigen presenting cells of peripheral blood lymphocytes of the subject; and
   iii. monitoring the extent of binding using phycoerythrin-avidin by flow cytometry.--

7. An assay in accordance with claim 6, wherein said peripheral blood lymphocytes consist of the adherent fraction thereof.--

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Asp Thr Pro Tyr Leu Asp Ile Thr Tyr His Phe Val Met Gln Arg Leu
1               5                   10                  15
Pro Leu ( 2 ) INFORMATION FOR SEQ ID NO:2:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( x i ) SEQUENCE DESCRIPTION: SEQ ID NO:2:

-continued

```
Leu Leu Val Ile Val Glu Leu Ile Pro Ser Thr Ser Ser Ala Val
 1           5                   10                      15
```